(12) United States Patent
Therre et al.

(10) Patent No.: US 6,559,346 B1
(45) Date of Patent: May 6, 2003

(54) METHOD FOR THE CONTINUOUS PRODUCTION OF GLUTARALDEHYDE

(75) Inventors: Jörg Therre, Worms (DE); Carsten Oost, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/069,770

(22) PCT Filed: Aug. 29, 2000

(86) PCT No.: PCT/EP00/08412

§ 371 (c)(1),
(2), (4) Date: Feb. 28, 2002

(87) PCT Pub. No.: WO01/16237

PCT Pub. Date: Mar. 8, 2001

(30) Foreign Application Priority Data

Aug. 30, 1999 (DE) .......................... 199 41 132

(51) Int. Cl.$^7$ ............................... C07C 45/42
(52) U.S. Cl. .................. 568/483; 568/484; 568/485
(58) Field of Search ................. 568/483, 484, 568/485

(56) References Cited

U.S. PATENT DOCUMENTS

| | | | |
|---|---|---|---|
| 2,546,018 A | * | 3/1951 | Smith et al. |
| 4,244,876 A | | 1/1981 | Warner et al. ............ 260/345 |
| 4,448,977 A | | 5/1984 | Warner et al. ............ 549/201 |
| 5,600,018 A | * | 2/1997 | Becker et al. |
| 5,679,868 A | * | 10/1997 | Kneuper et al. |

FOREIGN PATENT DOCUMENTS

| | | |
|---|---|---|
| EP | 0 066 224 | 12/1982 |
| JP | 7-226488 | 8/1995 |
| WO | WO 99/23088 | 5/1999 |

* cited by examiner

Primary Examiner—Johann Richter
Assistant Examiner—Sikarl A. Witherspoon
(74) Attorney, Agent, or Firm—Keil & Weinkauf

(57) ABSTRACT

In a process for the continuous preparation of glutaraldehyde by reaction of an alkoxydihydropyran of the formula I

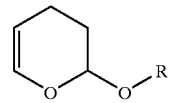

where R is $C_1$–$C_{20}$-alkyl, with water at from 0° C. to 200° C. and a pressure in the range from 0.01 bar to 16 bar to form glutaraldehyde and the alcohol corresponding to the alkoxy group, water and alkoxydihydropyran are fed continuously to a reaction column and a distillate enriched in the alcohol corresponding to the alkoxy group is taken off at the top of the column and a product enriched in glutaraldehyde is taken off at the bottom.

This process makes it possible to prepare glutaraldehyde or C-substituted glutaraldehydes continuously in high purity in a simple manner with a low outlay in terms of apparatus.

13 Claims, 2 Drawing Sheets

METHOD FOR THE CONTINUOUS PRODUCTION OF GLUTARALDEHYDE

This application is a 371 of PCT/EP00/08421, filed Aug. 28, 2000, published as WO 01/16237 on Mar. 8, 2001.

The present invention relates to a process for the continuous preparation of glutaraldehyde by reaction of alkoxydihydropyrans of the formula I

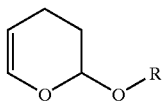

where R is a straight-chain or branched $C_1$–$C_{20}$-alkyl, preferably $C_1$–$C_8$-alkyl, in particular a methyl group, with water at from 0° C. to 200° C., preferably from 40 to 150° C., and a pressure in the range from 0.01 bar to 16 bar, preferably from 0.1 to 5 bar.

Glutaraldehyde is used, for example, as a microbiocide or in tanning.

U.S. Pat. No. 4,244,876 and the associated U.S. Pat. No. 4,448,977 describe storage-stable compositions comprising glutaraldehyde acetals and an organic acid as catalyst from which an aqueous solution of glutaraldehyde can be prepared quickly when required by addition of water. This solution is used, in particular, as biocide for the control of sulfur bacteria in oil wells. For this purpose, separation of the reaction mixture into its pure components is not necessary and the unpurified hydrolysis product is used. A 2-alkoxy-3,4-dihydropyran is reacted with an alcohol or glycol in the presence of an acid catalyst, e.g. a strong acid ion exchanger, to give a mixture of 2,6-dialkoxytetrahydropyran, dialkoxypentanal and 1,1,5,5-tetraalkoxypentane. After the ion exchanger has been separated off, an organic acid is added to the mixture. The resulting mixture is storage-stable. At the point of use, e.g. a drilling site, it can be converted into a glutaraldehyde-containing aqueous solution by addition of water.

The European patent application EP 0 066 224 A1 describes a process for preparing an essentially water-free glutaraldehyde precursor from which glutaraldehyde can be liberated within a short time by addition of water. To prepare the storage-stable precursor, a 2-alkoxy-3,4-dihydropyran is reacted with water in a molar ratio of from 1:1 to 3:1 at from 30 to about 100° C. in the presence of an acid catalyst, e.g. an acid ion exchanger. This gives a mixture comprising 2-hydroxy-6-methoxytetrahydropyran as main component together with traces of 2,6-dimethoxytetrahydropyran and glutaraldehyde. After the acid catalyst has been separated off, e.g. by filtration, the mixture is storage-stable. Addition of water results in hydrolysis to form glutaraldehyde. No provision is made for purifying the glutaraldehyde.

JP 72 26 488 discloses a process for the continuous preparation of glutaraldehyde by hydrolysis of a 2-alkoxy-3,4-dihydropyran in the presence of an acid catalyst. For this purpose, a mixture of the 2-alkoxy-3,4-dihydropyran and water in a molar ratio of from 1:2 to 1:100 is heated to from 50 to 200° C. The process is carried out so that a concentration of from 0.5 to 10% by weight of the 2-alkoxy-3,4-dihydropyran is maintained in the system. No provision is made for further purification. The reaction product obtained is used as tanning agent for leather.

U.S. Pat. No. 2,546,018 describes the synthesis of glutaraldehyde and C-substituted glutaraldehydes starting from dihydropyrans. The hydrolysis of the dihydropyran can be carried out in the presence or absence of acid catalysts, with an uncatalyzed reaction being preferred because of the simpler work-up of the mixture after the reaction. The reaction can be carried out batchwise, and it is also proposed that the alcohol formed be removed continuously from the reaction mixture during the reaction. It is also proposed that the reaction be carried out continuously. For this purpose, the reaction mixture is said to be passed through a tubular reactor which is heated to an appropriate temperature. The flow rate is selected so that the desired conversion has taken place at the outlet of the reactor. After the reaction mixture has left the reactor, it can either be collected first and then distilled batchwise or, as an alternative, a continuous distillation with the desired fractions being separated off is proposed. In each of the examples in this patent, the hydrolysis of the dihydropyran is carried out in a first step and a fractional distillation is subsequently carried out in a second step. A disadvantage of this process is that an elaborate apparatus is necessary, with the hydrolysis being carried out in a first stage using a first apparatus and the desired product being separated off by fractional distillation in a second stage using a second apparatus. This is cumbersome and incurs costs.

It is an object of the present invention to provide a process by means of which glutaraldehyde or C-substituted glutaraldehydes can be prepared continuously in increased purity in a simple manner, with the outlay for apparatus being kept as small as possible in order to keep production costs low.

We have found that this object is achieved by a process for the continuous preparation of glutaraldehyde by reaction of an alkoxydihydropropan of the formula I with water at from 0° C. to 200° C. and a pressure in the range from 0.01 bar to 16 bar to form glutaraldehyde and the alcohol corresponding to the alkoxy group, wherein water and alkoxydihydropyran are fed continuously to a reaction column, preferably at a point between the top and the bottom outlet of the reaction column, and a distillate enriched in the alcohol corresponding to the alkoxy group is taken off at the top of the column and a product enriched in glutaraldehyde is taken off at the bottom.

The apparatus used for the reaction can be very compact since the hydrolysis of the alkoxydihydropyran is carried out in the column and it is therefore not necessary to provide a separate vessel for carrying out the hydrolysis reaction. The continuous reaction mode significantly reduces the dimensions of the plant for the same throughput per unit time compared to a batchwise reaction with the alcohol formed and the glutaraldehyde being distilled off separately. Selection of appropriate reaction parameters or appropriate dimensions of the plant makes it possible to achieve virtually complete conversion of the alkoxydihydropyran, so that an increased yield can be achieved and the glutaraldehyde formed has a higher purity than that obtained in processes known hitherto.

The reaction rate can be increased by carrying out the reaction in the presence of an acid catalyst. Suitable acids are organic acids such as saturated and unsaturated carboxylic acids having from 1 to 10 carbon atoms. It is also possible to use polyfunctional acids such as maleic acid. Preference is given to using inorganic acids such as phosphoric acid, boric acid, nitric acid, sulfuric acid or acid salts, e.g. $NaH_2PO_4$. If acids which are not readily volatile under the operating conditions of the reaction column are used, they are preferably added in the upper part of the reaction column. When using acids which are volatile under the operating conditions, they can also be added in the lower or middle part of the reaction column. The amount of acid should be such that an acid concentration in the range from 0.0001% by weight to 10% by weight, in particular from 0.01% by weight to 3% by weight, is obtained in the stream leaving the bottom of the column. The catalysts are preferably used as solutions. Suitable solvents are water, alcohol, the alkoxydihydropyran or glutaraldehyde/water mixtures.

In place of liquid acids, catalytically active packing comprising solid acids can also be installed in the reaction column. Such solid acids are, for example, ion exchangers such as Amberlyst® 15 or the bleaching earth catalysts mentioned in DE 44 29 262. The catalysts are generally arranged in the column so that intimate contact of the reaction solution with the catalyst is possible but the solid catalyst is kept in place in the column by means of screens or filters. An example of such an arrangement is KATA-PAK® from Sulzer. Further solid catalysts which can be used are thin layer catalysts in the case of which a catalytically active composition has been applied directly to internals, ordered packing or random packing in the column, e.g. by impregnation and subsequent drying.

The reaction column preferably has at least 2, in particular at least 3, theoretical plates. In general, the number of theoretical plates is then in the range from 2 to 200, preferably from 3 to 100, in particular from 4 to 50.

The separation of the alcohol is further improved if the reaction column is operated under reflux and the reflux ratio is chosen so as to be in the range from 0.2 to 80, preferably from 0.4 to 40.

If the alcohol is distilled off at the top of the reaction column as an azeotrope with water, it is advantageous for the top of the reaction column to be connected to a phase separation vessel and for an aqueous phase which separates out to be returned to the top of the reaction column. In this case, additional runback to the column may be able to be dispensed with.

The heating power at the bottom of the column is preferably chosen so that the stream leaving the bottom of the column contains less than 10% by weight, preferably less than 1% by weight, of the alcohol liberated in the hydrolysis reaction.

The concentration of glutaraldehyde in the stream leaving the bottom of the column is from 5 to 75% by weight, preferably from 25 to 65% by weight.

Water and alkoxydihydropyran can be fed to the reaction column either separately or as a mixture. If they are fed in separately, the water is preferably introduced in the upper part of the reaction column. The alkoxydihydropyran is preferably introduced in the lower part of the reaction column. Between the point of introduction of the alkoxydihydropyran and the bottom of the reaction column and between this point and the top of the column there should in each case be sufficient theoretical plates so that the alkoxydihydropyran content of the bottom product and the top product, respectively, is within specification. This number of theoretical plates which are necessary depends on the reflux ratio and can easily be determined by preliminary tests. When water and alkoxydihydropyran are fed in as a mixture, they are generally introduced in the middle region of the reaction column.

The amount of alkoxydihydropyran introduced depends on the volume of the reaction column used, on the amount and type of catalyst and on the temperature in the reaction column and can easily be determined by preliminary tests. In general, from 1000 to 5000 kg/h of alkoxydihydropyran can be introduced per 1 $m^3$ of empty volume of the column.

The amount of water should be such that glutaraldehyde is obtained in the desired concentration at the bottom of the reaction column. In general, the molar ratio of water to alkoxydihydropyran is $\geq 3$, in particular $\geq 4$.

The reaction column can have various forms of packing or internals. Examples of such internals are random packing elements (e.g. Pall rings), structured packing made of sheet-metal (e.g. Sulzer Mellapak 250Y) or metal mesh (e.g. Sulzer BX or CY) or preferably trays (e.g. bubble cap trays, valve trays, tunnel trays) or else combinations of the internals mentioned. If appropriate, special residence trays having a particularly high liquid level or special constructions of the downflow shafts having a particularly large liquid content can also be used. Furthermore, packing comprising solid acids such as ion exchangers or bleaching earth catalysts can also be installed in the reaction column. Such packing is constructed so that intimate contact of the reaction solution with the catalyst is possible but the solid catalyst is kept in place in the column by means of screens or filters. An example of such an arrangement is KATAPAK from Sulzer.

The dimensions of the reaction column can be reduced if a side offtake for taking off a gaseous or preferably liquid product comprising water, alkoxydihydropyran and possibly the catalyst is provided in the middle section of the reaction column and the stream taken off at this point is conveyed to an associated reaction space, and the stream flowing out of the reaction space is recirculated to the reaction column, preferably in the middle region of the column and below the side offtake. The associated reaction space can be configured as a stirred vessel, a loop reactor or a tube reactor.

The amount of material taken off at the side offtake can vary within a wide range. It preferably corresponds to from 0.1 to 80 times, preferably from 0.2 to 30 times, the amount of alkoxydihydropyran fed to the reaction column.

Preference is given to feeding the water, the alkoxydihydropyran and, if appropriate, the catalyst into the associated reaction space.

The invention is illustrated below by means of examples and with reference to the accompanying drawing, without being restricted to these embodiments. Identical or corresponding parts are designated by the same reference numerals. In the drawing.

Figure 1:
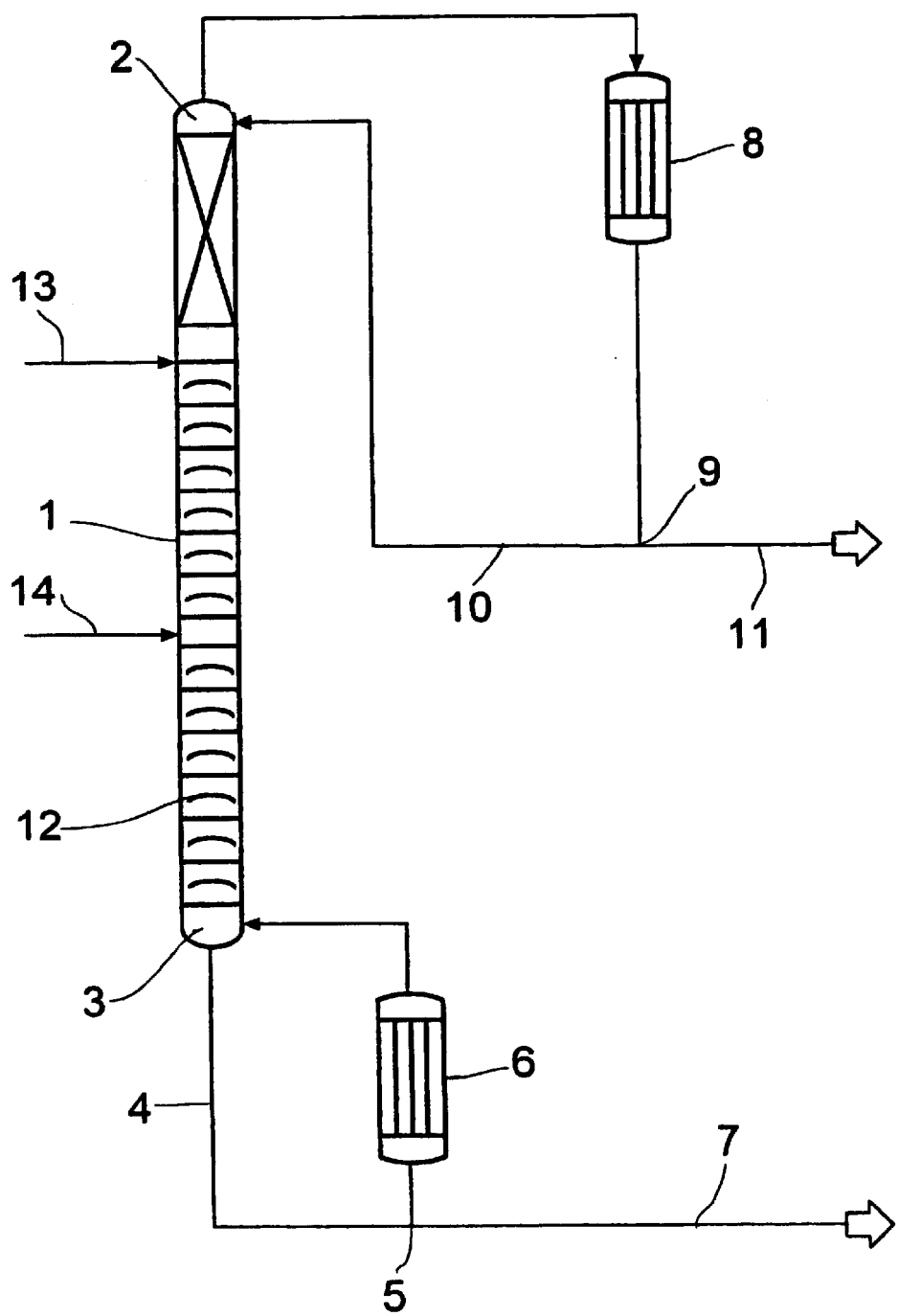
FIG. 1 shows a flow diagram of a first embodiment of an apparatus for carrying out the process of the present invention.

The apparatus shown in FIG. 1 comprises a reaction column 1 having a top 2 and a bottom 3. The column is provided with one of the above-described forms of packing. The stream leaving the bottom is conveyed via line 4 to a branch point 5 where part of this stream is vaporized again in a reboiler 6 and recirculated to the lower part of the column 1. Part of the stream from the bottom, which comprises glutaraldehyde in water, is taken off via line 7. At the top 3 of the reaction column 1, the distillate is conveyed to a condenser 8 and condensed. Part of the condensate is returned via the branch point 9 and the line 10 to the top 3 of the reaction column 1 as runback and part of the alcohol is discharged via line 11.

The water is fed via line 13, if appropriate in admixture with catalyst, to the upper part of the reaction column 1. The amount of water fed in is determined by the desired glutaraldehyde content of the aqueous solution taken off via line 7.

The alkoxydihydropyran is fed into the reaction column 1 via line 14. The location of the line 14 is chosen so that there are sufficient theoretical plates between the point of introduction of the alkoxydihydropyran and the bottom of the reaction column so that the alkoxydihydropyran content of the bottom product is within specification. Between the point of introduction of the alkoxydihydropyran and the top 3 of the reaction column 1, there should be sufficient theoretical plates for the alkoxydihydropyran content of the alcohol produced to be within specification.

Figure 2:
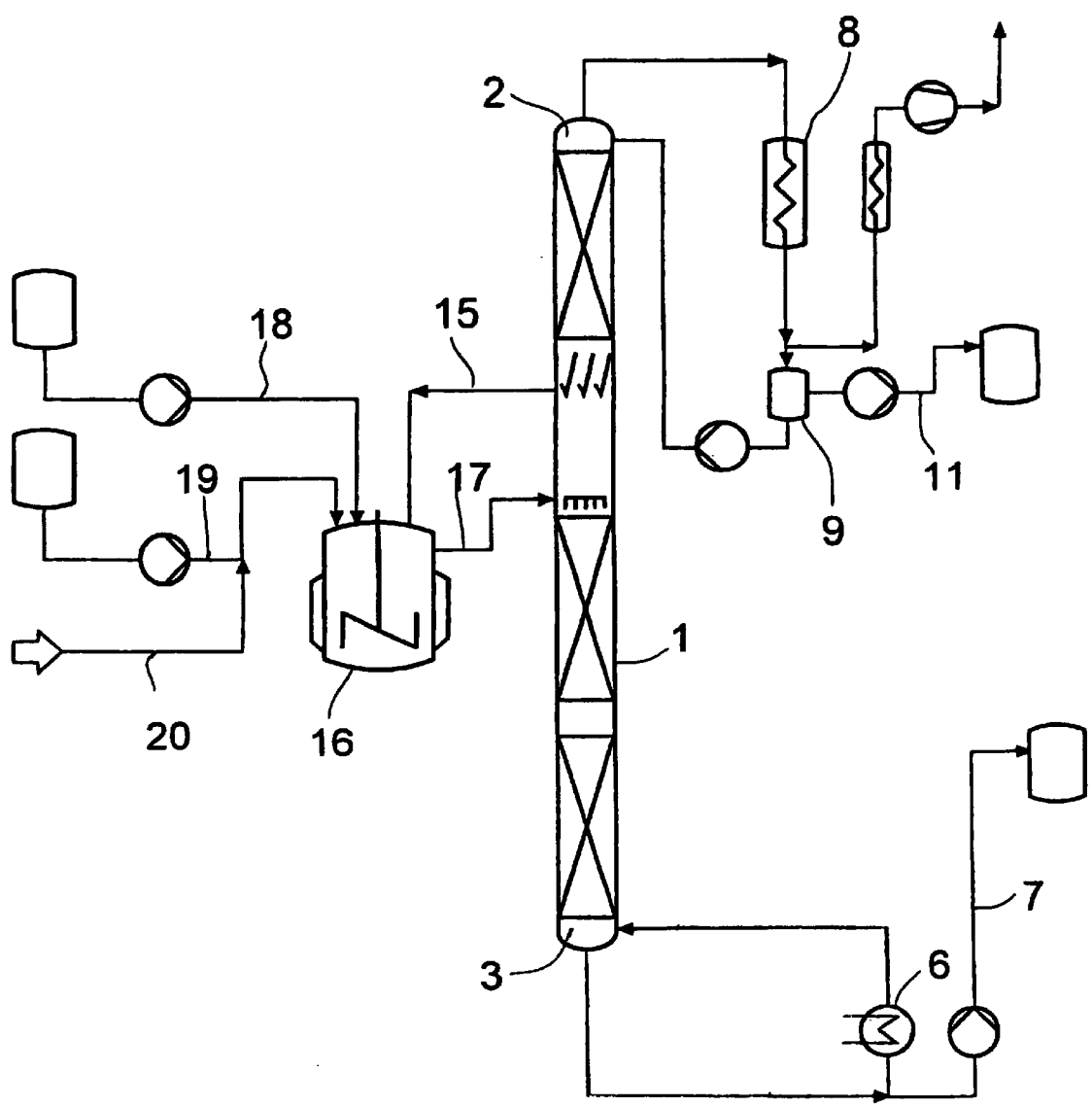
FIG. 2 shows a second embodiment of an apparatus for carrying out the process of the present invention.

FIG. 2 shows a second embodiment of an apparatus for carrying out the process of the present invention. As in the apparatus shown in FIG. 1, a reaction column 1 at the top 2 of which distillate is taken off and conveyed to a condenser 8 is provided. Part of the condensate is returned as runback to the top 2 of the column via the branch point 9 and part of it is discharged via line 11. At the bottom 3 of the reaction column 1, part of the stream leaving the bottom is vaporized again by means of the reboiler 6 and part is removed from the system via line 7.

A gaseous or preferably liquid side stream is taken from the reaction column 1 via line 15 and is conveyed to the vessel 16 located outside the reaction column 1. The vessel 16 is configured here as a stirred vessel, but it can also be configured as, for example, a loop reactor or tube reactor. The stream flowing from the vessel 16 is returned to the reaction column 1 via line 17. The alkoxydihydropyran and the water are fed to the vessel 16 via lines 18 and 19, with the line 20 for the introduction of the liquid catalyst opening into the water feed line 19.

EXAMPLE 1

In an apparatus as shown in FIG. 1, methoxydihydropyran (MOP) was saponified with water in a continuous reactive distillationto form glutaraldehyde and methanol. The reaction column was a tray column having 20 practical trays and an internal diameter of 50 mm and was operated at 400 mbar. 132 g/h of a 0.6 percent strength by weight solution of maleic acid in water were introduced onto the fourth tray from the top and 150 g/h of MOP were introduced onto the thirteenth tray from the top. The temperature at the top was maintained at 44° C. by changing the reflux ratio by means of an electronic runback distributor with boiling limit. The heating power of the reboiler 6 was regulated so that the temperature of the bottoms was 78° C. The bottoms comprised 44% by weight of water, 1.3% by weight of methanol and 54% by weight of glutaraldehyde. The distillate comprised 85% by weight of methanol, 1.5% by weight of water and 13.5% by weight of MOP.

EXAMPLE 2

In the apparatus described in Example 1 and operated at 400 mbar, 120 g/h of a 0.6% strength by weight solution of maleic anhydride 5 in water were introduced onto the sixth tray from the top and 147 g/h of MOP were introduced onto the twelfth tray from the top. A reflux ratio of 5:1 was set by means of an electronic runback distributor. The heating power of the reboiler 6 was regulated so that the temperature of the bottoms was 75° C. The bottoms comprised 43.85% by weight of water, 2.82% by weight of methanol and 53.33% by weight of glutaraldehyde. The distillate comprised 90.65% by weight of methanol, 1.16% by weight of water and 9.09% by weight of MOP.

EXAMPLE 3

An apparatus as shown in FIG. 1 was equipped with a reaction column comprising a bubble cap tray column having an internal diameter of 50 mm and 20 practical trays ontop of which a column section containing 50 cm of Sulzer DX packing was fitted. The pressure at the bottom of the column was 640 mbar, and the pressure at the top of the column was 595 mbar. 1380 ml/h of distillate were pumped as runback to the top of the column. 130 g/h of a 0.6 percent strength by weight solution of phosphoric acid in water were introduced onto the uppermost tray of the column and 150 g/h of MOP were introduced onto the thirteenth tray from the top of the bubble cap tray column. The heating power of the reboiler was regulated so that the temperature of the bottoms was 89° C. The bottoms comprised 48% by weight of water, 0.6% by weight of methanol, 0.5% by weight of MOP and 49% by weight of glutaraldehyde. The distillate comprised 96% by weight of methanol and 1.7% by weight of MOP.

EXAMPLE 4

An apparatus as shown in FIG. 2 comprised, as reaction column, a packed column whose lower part contained 96 cm of Sulzer CY packing and whose upper part was filled with 50 cm of Sulzer DX packing. A side offtake for liquid was located between the two column sections. The feed was introduced into the column 11 cm above the side offtake. The internal diameter of the column was 50 mm. The pressure at the bottom of the column was 619 mbar, and the pressure at the top of the column was 600 mbar. The reflux ratio at the top of the column was 17.3. At the side offtake of the column, 2440 ml/h of liquid were taken off and introduced into a reactor heated externally by means of oil to 74° C. The reactor was mixed by stirring and circulation of 1040 ml/h of liquid. The mass of reaction mixture in the reactor was 900 g. 150 g/h of MOP and 130 g/h of water were introduced into the reactor. 0.18% by weight of phosphoric acid was dissolved in the water. 45 g/h of distillate were taken off at the top of the column and 235 g/h of product were taken off at the bottom. The heating power of the reboiler was regulated so that the temperature of the bottoms was 87° C. The distillate comprised 99.05% by weight of methanol and 0.95% by weight of MOP. The bottoms comprised 47.3% by weight of water and 51% by weight of glutaraldehyde. The bottom product contained neither methanol nor MOP.

We claim:
1. A process for the continuous preparation of glutaraldehyde by reaction of an alkoxydihydropyran of the formula I

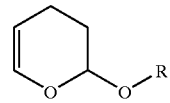

where R is $C_1$–$C_{20}$-alkyl, with water at from 0° C. to 200° C. and a pressure in the range from 0.01 bar to 16 bar to form glutaraldehyde and the alcohol corresponding to the alkoxy group of alkxoydihydropyran, comprising
   a) continuously introducing water and the alkoxydihydropyran into a reaction column at a point between the top and the bottom of the reaction column such that part of the theoretical plates is between the point of introduction and the bottom of the reaction column, and part of the theoretical plates is located between the point of introduction and the top of the reaction column; said reaction column having internals selected from the group consisting of random packing elements, structured packing made of sheet metal or metal mesh, trays and combinations thereof; the reaction column having at least 3 theoretical plates, and a reboiler at the bottom;
   b) taking off a distillate enriched in alcohol corresponding to the alkoxy group of the alkoxydihydropyran at the top of the column, and taking off a product enriched in glutaraldehyde at the bottom of the reaction column and c) controlling the heating power of the reboiler so that the product enriched in glutaraldehyde contains at least 10% by weight alcohol.

2. A process as claimed in claim 1, wherein the reaction is carried out in the presence of an acid catalyst.

3. A process as claimed in claim 1, wherein catalytically active packing comprising solid acids is installed in the reaction column.

4. A process as claimed in claim 1, wherein the amount of acid is such that an acid concentration in the range from 0.0001% by weight to 10% by weight, is obtained in the stream leaving the bottom of the reaction column.

5. A process as claimed in claim 1, wherein a reflux ratio in the range from 0.2 to 80, is set at the top of the reaction column.

6. A process as claimed in claim 1, wherein the heating power at the bottom of the reaction column is chosen so that the stream leaving the bottom of the column contains less than 10% by weight.

7. A process as claimed in claim 1, wherein the concentration of glutaraldehyde in the stream leaving the bottom of the column is from 5 to 75% b weight.

8. A process as claimed in claim 7, wherein the concentration of glutaraldehyde in the stream leaving the bottom of the column is from 26 to 65% b weight.

9. A process as claimed in claim 1, wherein the water and the alkoxydihydropyran are fed separately into the reaction column.

10. A process as claimed in claim 1, wherein a stream is taken off at a side offtake in the middle section of the reation column and is conveyed to a reaction space, and the stream flowing out of the readtion space is recirculated to the reaction column.

11. A process as claimed in claim 10, wherein the amount of material taken off at the side offtake corresponds to from 0.1 to 80 times the amount of alkoxydihydropyran fed to the reaction column.

12. A process as claimed in claim 4, wherein the amount of acid is such that an acid concentration in the range from 0.01% by weight to 30% by weight is obtained in the steam leaving the bottom of the reaction column.

13. A process as claimed in claim 5, wherein a reflux ratio in the range from 0.4 to 40 is set at the top of the reaction column.

* * * * *

UNITED STATES PATENT AND TRADEMARK OFFICE
CERTIFICATE OF CORRECTION

PATENT NO.      : 6,559,346 B1
DATED           : May 6, 2003
INVENTOR(S)     : Therre et al.

It is certified that error appears in the above-identified patent and that said Letters Patent is hereby corrected as shown below:

Column 7,
Line 25, "b weight" should be -- by weight --.

Column 8,
Line 3, "b weight" should be -- by weight --.
Line 19, "30%" should be -- 3% --.

Signed and Sealed this

First Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,559,346 B1
DATED : May 6, 2003
INVENTOR(S) : Therre et al.

It is certified that error appears in the above-identified patent and that said Letters Patent is hereby corrected as shown below:

<u>Column 7,</u>
Line 5, "at least" should be -- less than --;
Line 22, "10%" should be -- 1% --.

Signed and Sealed this

Sixteenth Day of March, 2004

JON W. DUDAS
*Acting Director of the United States Patent and Trademark Office*